United States Patent [19]

Gershoni

[11] Patent Number: 4,512,896

[45] Date of Patent: Apr. 23, 1985

[54] TRANSFER OF MACROMOLECULES FROM A CHROMATOGRAPHIC SUBSTRATE TO AN IMMOBILIZING MATRIX

[75] Inventor: Jonathan M. Gershoni, Hamden, Conn.

[73] Assignee: Yale University, New Haven, Conn.

[21] Appl. No.: 464,609

[22] Filed: Feb. 7, 1983

[51] Int. Cl.³ .................................. B01D 15/08
[52] U.S. Cl. ...................... 210/635; 210/645; 210/198.3; 210/502.1; 422/70
[58] Field of Search ............... 210/635, 645, 656, 658, 210/748, 198.3, 502.1; 422/70; 204/1 T, 180 P, 204/180 S, 180 G, 299 A

[56] References Cited

U.S. PATENT DOCUMENTS

| 3,875,044 | 4/1975 | Renn et al. ............... 210/198.3 |
| 3,878,100 | 4/1975 | Bixler ..................... 210/198.3 |
| 4,243,507 | 1/1981 | Martin et al. ............. 204/299 R |
| 4,297,198 | 10/1981 | Ohashi et al. ............. 204/180 S |
| 4,352,884 | 10/1982 | Nakashima et al. ........... 422/70 |
| 4,415,428 | 11/1983 | Nochumson et al. .......... 204/180 S |

FOREIGN PATENT DOCUMENTS 1213445 11/1970 United Kingdom ............ 210/198.3

OTHER PUBLICATIONS

Chromatographic and Allied Methods by Mikes, John Wiley & Sons of New York, pp. 663-667, 1979.

Primary Examiner—John Adee
Attorney, Agent, or Firm—Ostrolenk, Faber, Gerb & Soffen

[57] ABSTRACT

The method of transfer of macromolecules such as nucleic acid and proteins from a chromatographic substrate to an immobilizing matrix uses as the immobilizing matrix, a charge modified microporous membrane comprising an organic microporous membrane having a charge modifying amount of a cationic charge modifying agent bonded to substantially all of the wetted surfaces of said membrane. The charge modified microporous membrane can also be a reinforced microporous membrane, preferably a porous reinforcing web impregnated with a polymeric microporous membrane. A nucleic acid or protein blotting product comprising a chromatographic matrix having the charge modified microporous membrane on a surface thereof is also provided.

54 Claims, 6 Drawing Figures

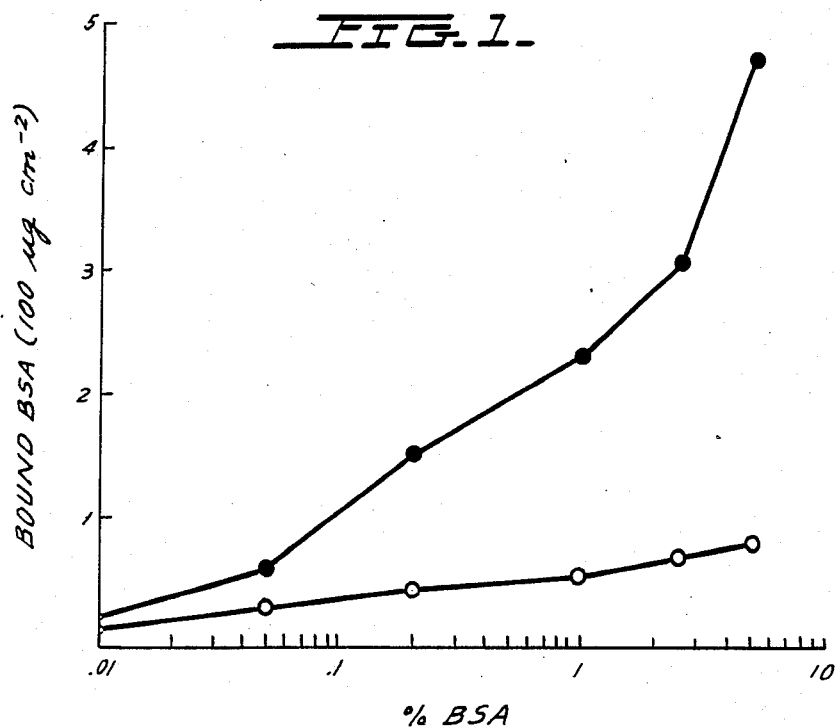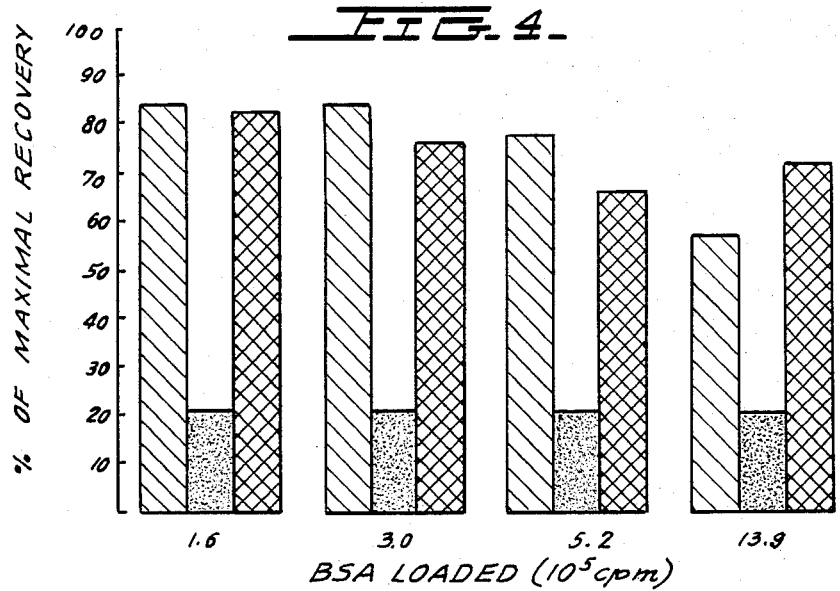

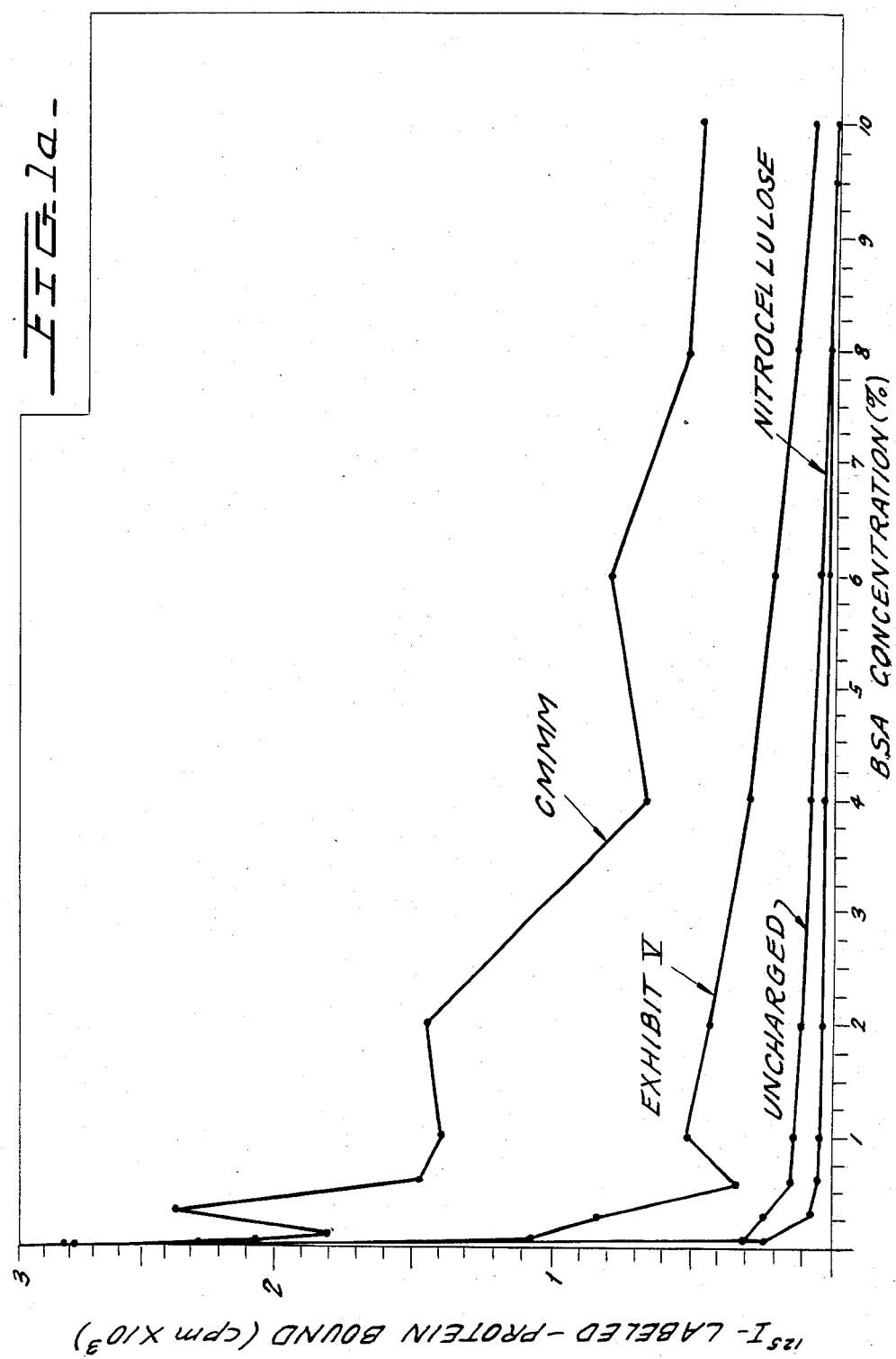

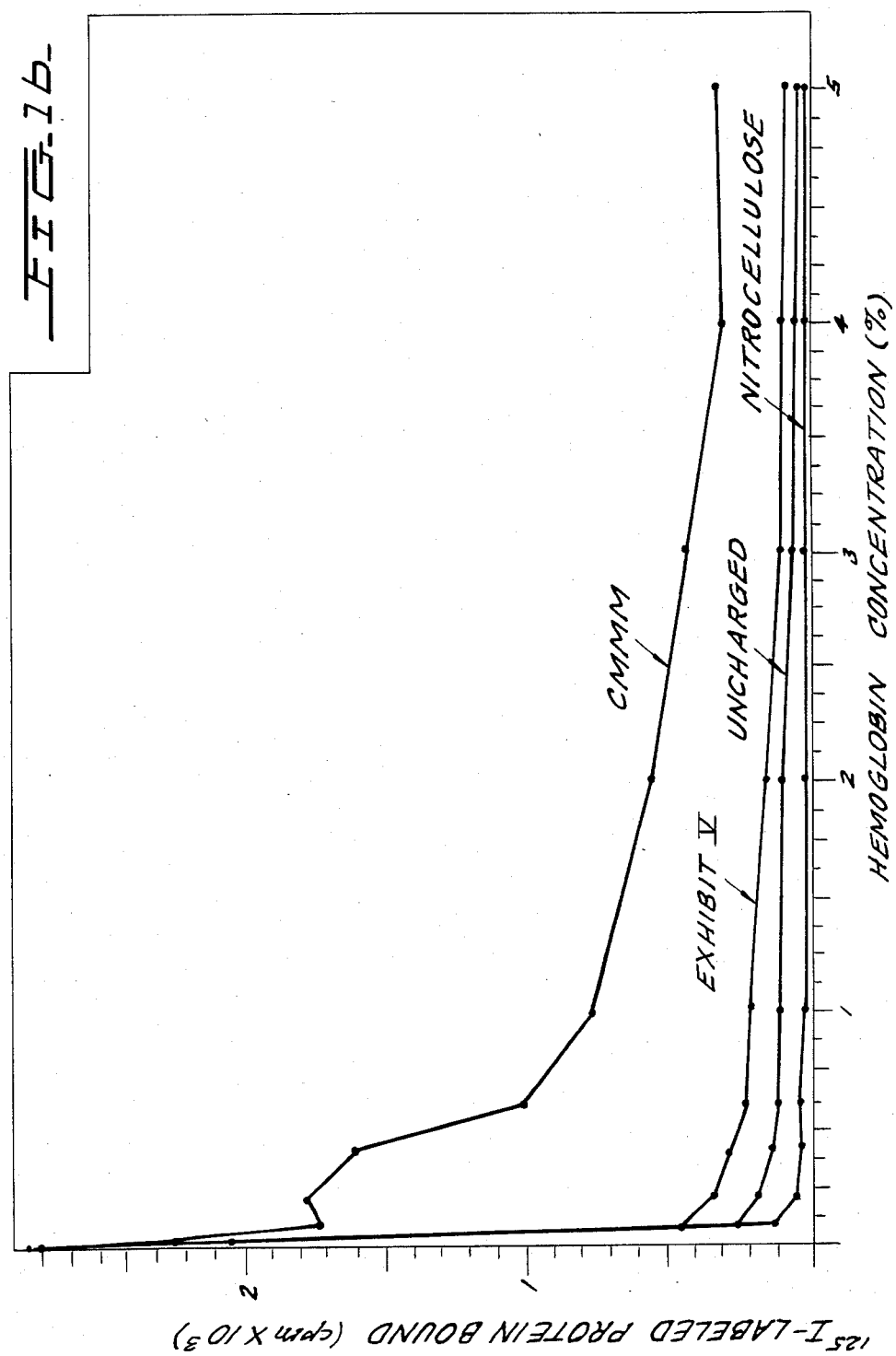

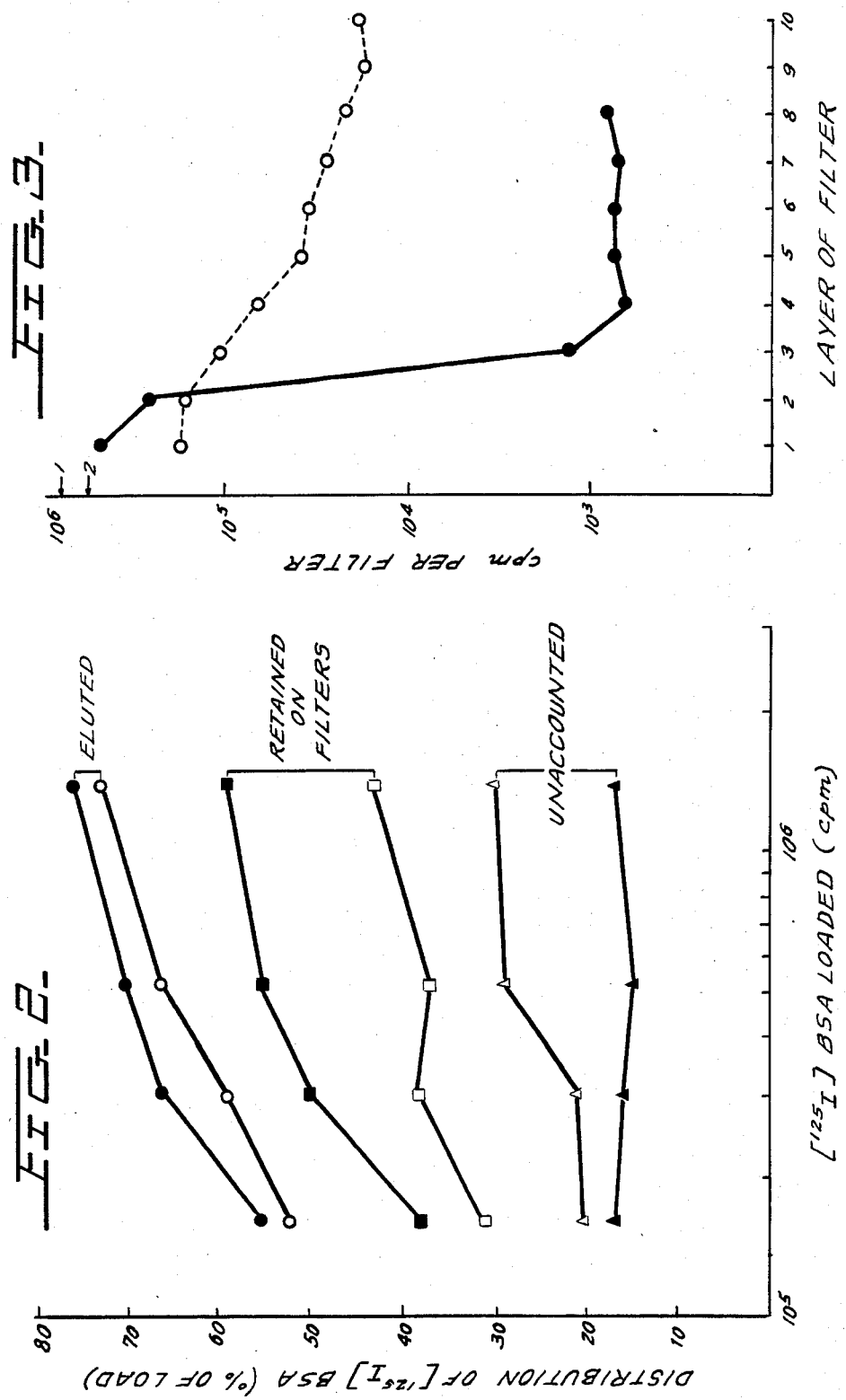

TRANSFER OF MACROMOLECULES FROM A CHROMATOGRAPHIC SUBSTRATE TO AN IMMOBILIZING MATRIX

BACKGROUND OF THE INVENTION

1. Field of the Invention

This invention relates to macromolecule blotting and more particularly to nucleic acid and protein blotting using a charge modified microporous membrane.

2. Prior Art

Smithies, Zone Electrophoresis in Starch Gels: Group Variations in the Serum Proteins of Normal Human Adults, Biochem. J. 61: 629–641 (1955), showed that starch gel could serve as a molecular sieve through which zone electrophoresis of proteins occur. Since then, there have been constant innovations in the technique of gel electrophoresis. The introduction of acrylamide gels, discontinuous buffer systems, the use of sodium dodecyl sulfate (SDS) to disaggregate protein complexes to be resolved on gels, and the eventual combined use of SDS in discontinuous buffer systems for polyacrylamide gel electrophoresis have been major contributions to the development of one of the most widely used analytical and preparative tools of modern biology.

The main objective of these techniques has been to visually demonstrate the homogeneity or complexity of a protein preparation by following the appearance or disappearance of a particular "band" throughout a given experimental procedure. One-dimensional gels were found to be adequate, provided only relatively simple protein samples such as viruses, bacteriophages, erythrocyte ghost membranes, etc., were being analyzed. More complex systems demanded greater resolving power and new two-dimensional gel systems were developed. Today, even the thousands of polypeptides which are a part of the more intricate proteinaceous samples can be efficiently resolved.

The task of unequivocally correlating a "band" or "spot" with a recognized function has often been difficult, and this is even more so when the resolution of the proteins depends on their denaturization. Nevertheless, many approaches have been developed which allow the identification of a specific enzyme or antigen or glycoprotein or hormone receptor, etc. in a gel. These techniques rely on the ability to maintain at least one of the following prerequisites: (1) that the polypeptides retain their activity throughout electrophoresis; (2) renaturation of a denatured polypeptide; and (3) covalent crosslinkage of the protein in question to a detectable ligand during electrophoresis. Moreover, the actual processing of the gels entails multiple manipulations and extensive incubations and washing procedures. This is very time consuming and quite often prone to handling accidents such as breakage and tearing of wet gels or cracking during the drying of the gels.

In order to try to overcome some of the problems encountered in analyzing gels, a new approach has evolved. A number of reports have been published demonstrating that the well established approach of "Southern-blotting", i.e. transferring DNA patterns from agarose gels to nitrocellulose membranes, can be applied to protein patterns in polyacrylamide gels. Intact protein patterns are eluted from the gels and are immobilized on a substratum. The substratum is, in turn, subjected to the same type of procedures which have been used on gels for "band" or "spot" identification.

However, by transferring electrophoretograms to immobilizing matrices one may benefit from the following advantages: (1) wet immobilizing matrices are pliable and easy to handle; (2) the immobilized proteins are readily and equally accessible to various ligands (since the limitations introduced in gels by differential porosity are obviated); (3) transfer analysis generally calls for small amounts of reagents; (4) processing times (incubations and washings) are significantly reduced; (5) multiple replicas of the gels may be made; (6) transferred patterns may be stored for months prior to their use; (7) protein transfers may undergo multiple analyses. Moreover, the transferred protein patterns are amenable to analyses which would be otherwise extremely difficult or impossible to perform on gels.

The term "blotting" today refers to the process of transferring biological macromolecules such as nucleic acids and proteins from gels to an immobilizing matrix. The term is often used in conjunction with the relevant macromolecule, e.g. protein blotting, DNA blotting and RNA blotting. The resulting matrix containing the transferred immobilized macromolecule is known as a "blot" or "transfer" and can be incubated with a ligand, a procedure which may be referred to as "overlay". Thus, for example, immunooverlay, lectin overlay or calmodulin overlay refers to the incubation of a blot with an antibody, lectin or calmodulin, respectively.

DNA blotting, a type of nucleic acid blotting, traces its origin to the technique often referred to as a "Southern Transfer" which was developed by Southern, Detection of Specific Sequences among DNA Fragments Separated by Gel Electrophoresis, J. Mol. Biol. 98: 503–517 (1975). After the chromatographic separation of the DNA fragments, the DNA is denatured while in the gel and the gel is neutralized. The gel is placed between wicking paper which is in contact with a buffer reservoir, nitrocellulose is placed on top of the gel and dry blotting papers are placed on top of the nitrocellulose. Mass flow of buffer through the gel elutes the DNA which then binds to the nitrocellulose. Thus, the electrophoretically separated DNA fragment pattern is transferred and preserved on the nitrocellulose. Hybridization with a specific labeled nucleic acid allows detection of the specific complementary fragments bound to the nitrocellulose.

In 1976, it was discovered that single stranded RNA and DNA could be covalently coupled to a cellulose powder substituted by aminobenzyloxymethyl groups which were activated by diazotizing the amine forming diazobenzyloxymethyl (DBM)—cellulose. This filled a gap in hyberdization technology since RNA does not bind well to nitrocellulose making a Southern Transfer difficult or impossible. In 1977, Alwine, et al., "Method for Detection of Specific RNAs in Agarose Gels by Transfer to Diazobenzyloxymethyl-Paper and Hybridization with DNA Probes, Proc. Natl. Acad. Sci. U.S.A., 74: 5350–5354, prepared a cellulosic fibrous sheet (i.e. blotting paper) derivatized with diazobenzyloxymethyl groups, termed DBM-paper, viz.

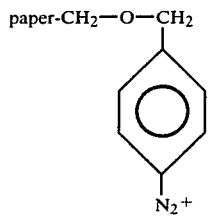

paper-CH₂—O—CH₂ ... N₂⁺ which could be used for transfer of an electrophoretically separated pattern of RNA from an agrose gel in a method similar to a Southern Transfer. Aminophenylthioether paper activated to the diazo form (DPT-paper) has also been used. Both papers covalently and irreversibly couple DNA, RNA and proteins.

DBM-paper and DPT-paper having the disadvantages that they require activation, have limited life, i.e. their activity is labile, having binding capacity only comparable to nitrocellulose, irreversibly couples the macromolecules, thus preventing their subsequent elution, and may present difficulties in resolution due to the texture of the surface.

In an effort to overcome some of the inconveniences of DBM paper, Thomas, (1980) developed a technique to transfer RNA and small DNA fragments to nitrocellulose using high salt concentrations. The binding efficiency of RNA was found to be 80 ug/cm² as compared to 35 ug/cm² for DBM paper. Elution of macromolecules from polyacrylamide gels can be accomplished efficiently by electrophoresis. However, the requirement of high salt concentrations would lead to impractically high currents.

Although first developed in connection with the study of DNA and RNA, it became recognized that the blotting techniques pioneered by Southern could be applied to proteins. The protein transfer techniques were first developed by Renart, Transfer of Proteins from Gels to Diazobenzyloxymethyl-Paper and Detection with Antisera: A Method for Studying Antibody Specificity and Antigen Structure, *Proc. Natl. Acad. Sci. U.S.A.* 76: 3116–3120 (1979), who achieved protein transfer to DBM paper using composite agarose-acrylamide gels in which the acrylamide crosslinking agent was reversible. After electrophoresis, the crosslinking was removed, leaving a low percentage agarose gel from which the proteins transferred easily. Shortly thereafter, a protein blotting procedure was developed by Bowen et al., The Detection of DNA-Binding Proteins by Protein Blotting, *Nuc. Acids Res.* 8: 1–20 (1980), using nitrocellulose for the transfer of DNA binding and other ligand-binding proteins separated on SDS-polyacrylamide gels. In this procedure, transfer was accomplished by diffusion. Towbin, et al. (1979) *Proc. Natl. Acad. Sci. USA* 76: 4350–4354 and Bittner, M. et al. (1980) *Anal. Biochem.* 102: 459–471 had demonstrated that transfer could be accomplished electrophoretically even at low salt concentrations.

In general, protein blotting should be viewed as two sequential events, namely the elution of the polypeptide from the gel and the adsorption of the eluted material to an immobilizing matrix.

Three main driving forces have been exploited for macromolecule elution. One is diffusion. Here, the gel containing the macromolecules to be transferred is sandwiched between two sheets of immobilizing matrix which are in turn sandwiched between foam pads and stainless steel screens. This final assembly is then submerged in two liters of buffer and allowed to sit for 36–48 hours. The result of this incubation is that two identical replica blots are obtained. The efficiency of transfer may reach 75%, but this value must be divided between the two replicas. If the amount of macromolecule adsorbed onto the matrix is sufficient for the intended assays and the long transfer time is not detrimental, blotting by diffusion can be useful.

The second means of macromolecule blotting is essentially based on mass flow of liquid through the gel in the same manner DNA blots are achieved in the traditional procedure described by Southern. The gel is placed in a reservoir of buffer. A matrix is applied to the gel and paper towels are piled onto the matrix. The towels absorb the buffer from the reservoir through the gel and matrix. This movement of fluid serves as a driving force which elutes the proteins out of the gel which are then trapped in the filter. This technique is less time consuming than diffusion blotting and the efficiency of elution is better. A modification of this approach has been suggested which allows bidirectional blotting. Moreover, the time for efficient elution has been dramatically reduced by applying a vacuum to facilitate the process.

The most widely used mode for protein blotting is based on electroeluting the proteins from gels. This is made possible due to the fact that proteins, in contrast to DNA, adsorb the nitrocellulose even in low ionic strength buffers (when other immobilizing matrices are used, e.g. DBM paper, this is no longer a consideration). Therefore, one can electrophorese the proteins out of the gel without generating intolerable currents. It should be noted that the concept of electroelution of macromolecules for blotting was originally described by Arnheim and Southern in 1977 (Heterogeneity of the Ribosomal Genes in Mice and Men, *Cell* 11: 363–370). Numerous apparatus designs have been reported and quite a few are now commercially available. In essence, a wet matrix material is placed on a gel, making sure that no air bubbles are caught within the filter or between the matrix and the gel. The matrix and gel are then sandwiched between supportive porous pads such as "Scotch Brite" scouring pads, foam rubber or layers of wet blotting paper. The assembly is then supported by solid grids (usually nonconductive). It is very important that the gel and matrix are firmly held together. This ensures good transfer and prevents distortion of the protein bands. The supported "gel+matrix sandwich" is inserted into a tank containing "transfer buffer" and placed between two electrodes. The electrodes, which may be tacked to the sides of the tank, are designed so as to generate a homogeneous field over the entire area of the gel which is to be transferred. Continuous conductive sheets can serve as electrodes and theoretically are most appropriate for this purpose. Slabs of graphite and stainless steel plates have been used. However, operating units with such electrodes is usually impractical due to the requirement for excessively high currents. Some apparatus use stainless steel mesh or platinum mesh. An economical, yet efficient, design that seems to work reasonably well is that described by Bittner et al (Electrophoretic Transfer of Proteins and Nucleic Acids from Slab Gels to Diazobenzyloxymethyl Cellulose or Nitrocellulose Sheets, *Ana. Biochem.* 102: 459–471). Factors that may influence the homogeneity of the field are the distance between the gel and the electrode and the density of the electrode material i.e. the distance between each stretch of wire used. In general, the more electrode material present the lower the electrical resistance of the system. This, therefore, demands higher currents in order to obtain reasonable voltage differences to drive the elution process. The transfer buffers used can be of low ionic strength, such as a phosphate buffer, Tris-borate buffer or Tris-glycine and may or may not contain methanol. Methanol tends to increase the binding capacity of nitrocellulose for protein and stabilize the geometry of the gel being transferred but reduces the elution efficiency of protein from SDS gels and in its presence, electroelution must be carried out for long durations, generally more than 12 hours, in order to obtain efficient transfer of high molecular weight proteins. In the absence of methanol, gels of acrylamide tend to swell and, if allowed to occur during protein transfer, causes the band to be distorted.

The conditions of transferring per se are dependent on the type of gel, the immobilizing matrix and the transfer apparatus used as well as the macromolecules themselves. Nondenaturing gels, SDS gels, lithium dodecyl sulfate containing gels, iso-electrofocusing 2D gels and agarose gels have all been used for protein blotting. It is necessary to determine the electric charge of the protein to be eluted and place the matrix on the appropriate side of the gel. Proteins from SDS-gels, for example, are eluted as anions and therefore the matrix should be placed on the anode side of the gel. The case may be the opposite for nondenaturing gels. As electroelution progresses, electrolytes from the gel are also eluted and contribute to the conductivity of the buffer, resulting in a drop in resistance. Were one to conduct the transfer at constant voltage, the current would increase accordingly and currents in excess of one ampere, and indeed up to five amperes, may develop. High current (one to five ampere) power supplies are not commercially available for electroblotting. Another alternative has been to use a 12 V battery charger which seems to be quite adequate. However, as most of the common power supplies used for gel electrophoresis cannot exceed 200-250 mA, it has been found advantageous to run at a maximal constant current (i.e. 200 mA) and allow the voltage to gradually drop during the transfer.

There are incidences where isolated proteins of low or moderate molecular weight do not elute efficiently from a gel. This can occur in those cases where these proteins fortuitously are at their isoelectric point and have no tendency to migrate in the electric field exerted. In such an instance, other buffer conditions can be employed.

There are numerous immobilizing matrices which are available today. While nitrocellulose is the most widely used material as a matrix, the interaction of a protein with the nitrocellulose is complex and not clearly understood. For example, at pH 8 where protein electroelution is usually performed, nitrocellulose is negatively charged as are the proteins being adsorbed. Hydrophobic effects play a role in this interaction and indeed, protein elution from the matrix is facilitated by non-ionic detergents. Some proteins, especially those of low molecular weight, bind with low affinities to nitrocellulose and may be lost during transfer or subsequent processing. To prevent such a loss, the transferred polypeptide can be crosslinked to the matrix, thereby covalently stabilizing the protein pattern. The presence of cellulose acetate in nitrocelluloe membrane matrices seems to reduce their capacity to bind protein. However, cellulose acetate matrices have been employed successfully for protein blotting.

In order to remedy some of the disadvantages of nitrocellulose matrices, alternative immobilizing matrices have been proposed. Transfer to DBM paper results in a covalently bound and stable protein pattern. Resolution is slightly lower on this material due to its intrinsic coarseness as compared to membrane matrices. Also, glycine, a commonly used material in transfer buffers, can interfere with DBM paper protein blotting. There still remains, therefore, a need for an immobilizing matrix which overcomes the disadvantages of the nitrocellulose, DBM paper and other matrices which have been used heretofore. A greater transfer capacity is also desirable.

It is known in the art that membranes may be used in chromatography in general and electrophoresis in particular. See, for example, U.S. Pat. Nos.:

3,808,118 to Golias
3,829,370 to Bourat
3,945,926 to Kesting
3,957,651 to Kesting
3,989,613 to Gritzner
4,043,895 to Gritzner
4,111,784 to Dahms
4,158,683 to Del Campo
4,204,929 to Bier
4,243,507 to Martin
4,310,408 to Roe and
4,311,574 to Ishikawa Additionally, it is known that polyamide powders may be used to perform chromatographic separations. See, e.g. U.S. Pat. Nos.:

3,418,158 to Perry and
3,523,350 to Goldberg.

Hiratsuka et al., U.S. Pat. No. 4,128,470, teaches that nylon microporous membranes may be used in electrophoresis and isoelectric focusing as the medium through which chromatography is performed.

New England Nuclear has been marketing an uncharged nylon membrane for use in blotting in its "Gene Screen" electrophoresis product line. This material appears to have equivalent binding capacity for proteins as nitrocellulose.

3. Utility

Macromolecule blots or transfers can be "overlaid" with a variety of reagents in much the same manner that has been developed for gels. Manipulation of filter matrices is less time consuming, more economical with respect to the reagents used and is less exposed to handling accidents. More important, however, is the fact that transferring proteins from gels to matrices in effect eliminates diffusion barriers. Furthermore, denatured polypeptides can sometimes be renatured upon removal of SDS from them and this process is probably much more convenient and effective using blots.

Presently, most of the probes which have been used are macromolecules which specifically bind well to defined domains of the polypeptides under investigation. Lectins have allowed the detection of glycoproteins and antibodies and the identification of their corresponding antigens. Regardless of what the intended assay may be, vacant areas of the matrix which do not contain protein bands can non-specifically adsorb probes during the overlay process leading to intolerable background. Therefore, the unbound sites of the matrix must be quenched prior to overlaying the blot. Quenching is most commonly achieved by incubating the blot in high concentrations of bovine serum albumin (BSA) or hemoglobin at 25°–60° C. for 1–12 hours. Other materials such as ovalbumin, gelatin and various animal sera have also been used. The temperature, choice of protein and duration of quench depend on the type of matrix material and the probe being used. Non-ionic detergents have also been included in quench or washing buffers to reduce non-specific binding.

Once the blot has been quenched, it is reacted with the probe. In general, all reactions should be carried out in the presence of quenching protein. The reacted blot is then washed extensively in buffer (which does not have to contain protein). If the probe is itself radioactive or conjugated to an enzyme or fluorescent tag, the blot can be immediately autoradiographed, reacted with the relevant substrate or visualized in UV light, respectively. If further second or third reagents are necessary to detect the presence of probe-band complexes, then each consecutive reagent is incubated with the blot followed by a wash. The great sensitivity of these overlay techniques has allowed the detection of very low amounts (e.g. 1 ng) of viral antigens in natural fluids. Furthermore, these techniques have also been employed in the analysis of human sera of patient suffering from various immune disorders.

One of the advantages of blots over gels is that they may be reused or subjected to multiple reactions. Once a signal has been obtained and recorded, the blot may be "erased" by removing the probe but retaining the original protein pattern on the matrix. The "erased" filter can be reused for additional overlay analysis for further characterization of the elements of the gel pattern. "Erasing" can be accomplished by dropping the pH to dissociate antibody-antigen complexes or by denturing the probe by incubating the blot in urea or SDS. Selective dissociation of probe-band complexes, demonstrating specificity, may also be achieved. Lectins can be selectively competed off with relevant haptens. Calmodulin can be dissociated from calmodulin binding proteins by removing Ca++ from the system. These reactions can still be performed even after the protein blot has been autoradiographed to obtain the initial signal.

Use of protein blots usually has the objectives of demonstrating protein-protein or protein-ligand interactions or of exploiting the production of an immobilized polypeptide as an intermediate step in immunological or biochemical analyses. Both of these approaches have been exploited in novel usages of protein blots. For example:

a: Analysis of protein-ligand associations.

DNA-protein and RNA-protein interactions have been analyzed by protein blots. Histone H2 associations with H3 and H4 have also been demonstrated.

The epidermal growth factor receptor was identified by hormone overlaying a transferred membrane pattern. Membranes from human epidermoid carcinoma cells (A-431) were prepared and run on SDS-polyacrylamide gels. The gels were then electroblotted onto DBM paper, quenched and overlaid with epidermal growth factor and subsequently with radioactively labeled antibody to the hormone. One very predominant signal at 150 KD was detected.

b: Identification of enzyme subunits.

The detection of an inactive enzyme on a protein blot has been demonstrated. Phosphodiesterase I, for example, was boiled in 2% SDS for 5 minutes and run on a SDS-polyacrylamide gel. Protein was blotted into nitrocellulose filters which were reacted with excess anti-phosphodiestrase I. The matrix was then incubated with a crude preparation containing active enzyme. The active enzyme bound via unoccupied sites of the antibody to the inactivated resolved subunit immobilized on the matrix. The matrices were then reacted for enzyme activity and the immunocomplexes were thus detected.

c: Affinity purification of monospecific antibodies.

Blots have been used for the purification of monospecific antibodies. Polypeptides are resolved on SDS-polyacrylamide gels and blotted onto DBM or CNBr paper. The matrices were overlaid with serum containing polyclonal antibodies. Then single bands containing antigen-antibody complexes were excised from the matrices from which the monospecific antibody was eluted by incubating the strip in low pH (2–3) buffer. The eluted probe could then be used for immunocytochemical localization studies.

d: Demonstration of cell-protein interactions.

Protein blots have been used to demonstrate specific whole cell-polypeptide interactions. Human plasma was run on SDS-polyacrylamide gels and transferred to nitrocellulose matrices. Once the matrices were quenched, they were incubated with normal rat kidney cells (NRK cells) which specifically bound to immobilized polypeptides presumably involved in cell attachment. The cells were stained with amino black and were found to locate themselves at two discrete bands. These bands were identified as: fibronectin and a newly discovered 70 KD entity.

OBJECTS AND SUMMARY OF THE INVENTION

It is an object of this invention to provide a new immobilizing matrix for use in macromolecule blotting with increased versatility, adsorbence and retention compared to known materials.

It is another object of this invention to provide an immobilizing matrix for macromolecule blotting which provides for the more efficient transfer of macromolecules to the matrix and overcomes various deficiencies of the prior art matrices.

It is a further object of this invention to provide a method for the electrophoretic transfer of proteins from an electrophoresis gel to an immobilizing matrix which has better adsorbence and retention than prior art material such as nitrocellulose, and does not require high salt concentrations in the transfer buffer.

It is yet another object of this invention to provide a macromolecule blotting product of a chromatographic substrate and an immobilizing matrix which has better capacity and adsorbence than prior art macromolecule blotting products.

It is still another object of this invention to provide a macromolecule blotting product and procedure on which overlay techniques can be efficiently carried out.

These and other objects of the invention are achieved by using as the immobilizing matrix, a charge modified microporous membrane which comprises a hydrophilic organic microporous membrane having a charge modifying amount of a cationic charge modifying agent bonded to substantially all of the wetted surfaces of the membrane. Preferably, the cationic charge modifying agent is a water-soluble organic polymer having a molecular weight greater than about 1,000, wherein each monomer thereof has at least one epoxide group capable of bonding to the surface of the membrane and at least one tertiary amine or quaternary ammonium group. Most preferably, a portion of the epoxy groups on the organic polymer are bonded to a secondary charge modifying agent which is an aliphatic amine having at least one primary amino or at least two secondary amino groups or an aliphatic amine having at least one secondary amino group and a carboxyl or hydroxyl substituent.

The charge modifying agent can also be an aliphatic amine or polyamine bonded to the membrane through a cross-linking agent which is an aliphatic polyepoxide having a molecular weight of less than about 500.

The preferred microporous membrane is nylon. The charge modified microporous membrane can be employed in the form of a reinforced laminated membrane or preferably a porous reinforcing web impregnated with a polymeric microporous membrane.

BRIEF DESCRIPTION OF THE FIGURES

FIG. 1 illustrates the binding of $^{125}I$-labeled BSA to a membrane used in this invention and a matrix of the prior art.

FIG. 1a illustrates the effect of variable concentrations of BSA on the binding of $^{125}I$-labeled proteins to IMs.

FIG. 1b illustrates the effect of variable concentrations of bovine hemoglobin on the binding of $^{125}I$-labeled proteins to IMs.

FIG. 2 is a quantification of transfer of variable amounts of $^{125}I$-labeled BSA to the matrices of FIG. 1.

FIG. 3 shows the recovery of $^{125}I$-labeled BSA on successive layers of the matrices of FIG. 1.

FIG. 4 is a comparison of BSA recovery on layers of the matrices of FIG. 1.

DETAILED DESCRIPTION OF THE INVENTION

The immobilizing matrix of this invention is a hydrophilic charge modified microporous membrane comprising an organic microporous membrane having a charge modifying amount of a cationic charge modifying agent bonded to substantially all of the wetted surfaces of the membrane. Microporous membranes and cationic charge modified membranes are well known in the art for the filtration of fluids, e.g. liquids. The cationic charge modified microporous membranes, their preparation and such use in the filtration of fluids are described and claimed in U.S. patent application Ser. No. 268,543, filed on May 29, 1981, in the name of Barnes et al., now U.S. Pat. No. 4,473,475, and EPC Pub. Nos. 0066 814 and U.S. patent application Ser. No. 314,307, filed on Oct. 23, 1981 in the name of Ostreicher et al., now U.S. Pat. No. 4,473,474 and EPC Pub. Nos. 0050 864 in the name of Barnes et l. describes the use of charged modified membrane for the filtration of high purity water (18 megohm-centimeter resistivity) used in the electronics industry; and Ostreicher et al describes the use of charged modified membrane for the filtration of parenteral or body liquids. Additionally, it should be noted that these filter membranes may be reinforced by various means. A unique method of reinforcement is described in U.S. patent application Ser. No. 332,068, filed Dec. 18, 1981 in the name of Barnes et al. The disclosures thereof are hereby incorporated by reference.

Additionally, commercially available nylon microporous filter membranes are available from Pall Corp., Glen Cove, NY under the trademark ULTIPOR $N_{66}$ and $N_{66}$ POSIDYNE, the latter being a cationically charged modified filter membrane.

Additionally, AMF Inc., Cuno Div., is selling cationically charged modified nylon microporous filter membrane under the trademark ZETAPOR.

By the use of the term "microporous membrane" as used herein, it is meant a preferably substantially symmetrical and isotropic porous membrane having a pore size of at least 0.05 microns or larger or an initial bubble point (IBP), as that term is used herein, in water of less than 120 psi. The pore size can be up to about 1.2 micron or an IBP of greater than about 10 psi. By "symmetrical" it is meant that the pore structure is substantially the same on both sides of the membrane. By the use of the term "isotropic", it is meant the membrane has a uniform pore structure throughout the membrane.

The membrane is preferably hydrophilic. By the use of the term "hydrophilic" in describing the microporous membrane, it is meant a membrane which adsorbs or absorbs water. Generally, such hydrophilicity is produced by a sufficient amount of hydroxyl (—OH), carboxyl (—COOH) amino (—NH$_2$) and/or similar functional groups on the surface of the membrane. Such groups assist in the adsorption and/or absorption of the water onto the membrane. Such hydrophilicity of the immobilizing matrix is a necessary element of this invention. Hydrophilicity of the membrane per se provides adequate bonding of the charge modifying agent to the microporous membrane.

A preferred microporous membrane is one produced from nylon. The term "nylon" is intended to embrace film forming polyamide resins including copolymers and terpolymers which include the recurring amido grouping.

While, generally, the various nylon or polyamide resins are all copolymers of a diamine and a dicarboxylic acid, or homopolymers of a lactam of an amino acid, they vary widely in crystallinity or solid structure, melting point, and other physical properties. Preferred nylons for use in this invention are copolymers of hexamethylene diamine and adipic acid (nylon 66), copolymers of hexamethylene diamine and sebacic acid (nylon 610), and homopolymers of poly-o-caprolactam (nylon 6).

Alternatively, these preferred polyamide resins have a ratio of methylene (CH$_2$) to amide (NHCO) groups within the range about 5:1 to about 8:1, most preferably about 5:1 to about 7:1. Nylon 6 and nylon 66 each have a ration of 6:1, whereas nylon 610 has a ratio of 8:1.

The nylon polymers are available in a wide variety of grades, which vary appreciably with respect to molecular weight, within the range from about 15,000 to about 42,000 and in other characteristics.

The highly preferred species of the units composing the polymer chain is polyhexamethylene adipamide, i.e. nylon 66, and molecular weights in the range above about 30,000 are preferred. Polymers free of additives are generally preferred, but the addition of antioxidants or similar additives may have benefit under some conditions.

The preferred membrane substrates are produced by the method disclosed in U.S. Pat. No. 3,876,738 to Marinaccio et al. Another method of producing such membranes is described in European Patent Application No. 0 005 536 to Pall. The entire disclosures of both of these references are incorporated herein by reference.

Additionally, any of the hydrophilic microporous membranes commercially available, for example, Pall Corp.'s ULTIPOR $N_{66}$ (nylon), Millipore's Durapore (polyvinylidene fluoride), and cellulose acetate/nitrate membranes produced by numerous companies, are suitable for cationic charge modifying for use in accordance with this invention.

The preferred nylon membranes, i.e. described in Marinaccio et al. and Pall, are characterized by an isotropic structure, having a high effective surface area and a fine internal microstructure of controlled pore dimensions with narrow pore size distribution and adequate pore volume. For example, a representative 0.22 micrometer rated nylon 66 membrane (polyhexamethylene adipamide) exhibits an initial bubble point (IBP) of about 45 to 50 psid., a foam all over point (FAOP) of about 50 to 55 psid, provides a flow of from 70 to 80 ml/min of water at 5 psid (47 mm. diameter discs), has a surface are (BET, nitrogen adsorption) of about 13 $m^2/g$ and a thickness of about 4.5 to 4.75 mils.

The charge modifying agent is bonded to substantially all of the wetted surface of the microporous membrane. By the use of the term "bonded", it is meant that the charge modifying agent(s) are sufficiently attached to the membrane and/or to each other so that they will not significantly extract under the intended conditions of use. The term "substantially all of the wetted surface" as used herein means that all of the external surface and internal pore surfaces which are wetted by a fluid passing through the membrane or in which the membrane is immersed.

One preferred charge modifying agent which can be used in this invention is described in Ostreicher et al. and is a water-soluble organic polymer having a molecular weight greater than about 1,000, wherein the monomer has at least one epoxide substituent capable of bonding to the surface of the membrane and at least one tertiary amine or quaternary ammonium group capable of providing a cationic charge site. Preferably, this charge modifier is a polyamido-polyamine epichlorohydrin cationic resin, in particular, those described in the following U.S. Pat. Nos.

2,926,116 to Keim
2,926,154 to Keim
3,224,986 to Butler et al.
3,311,594 to Earle, Jr.
3,332,901 to Keim
3,382,096 to Boardman
3,761,350 to Munjat et al.

The entire disclosures of all of these references are incorporated herein by reference.

The preferred polyamido-polyamine epichlorohydrin cationic resins are available commercially as Polycup 172, 1884, 2002 or S 2064 (Hercules); Cascamide Resin pR-420 (Borden); or Nopcobond 35 (Nopco). Most preferably, the polyamido-polyamine epichlorohydrin resin is Hercules R 4308, wherein the charged nitrogen atom forms part of a heterocyclic grouping, and is bonded through a methylene moiety to a depending, reactive epoxide group.

Each monomer group in R 4308 has the general formula:

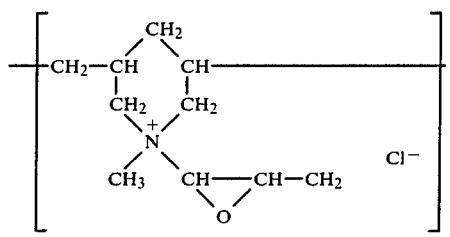

Polycup 172, 2002 and 1884, on the other hand, have monomer groups of the general formula:

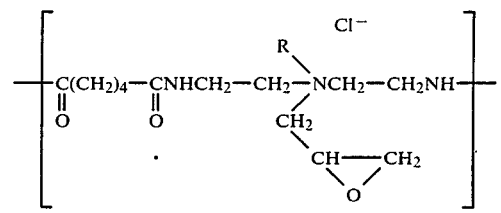

wherein R is methyl or hydrogen (Polycup 172 and 2002, R=H; and Polycup 1884, $R=CH_3$).

Most preferably, when the charge modifying agent is a water-soluble organic polymer having a molecular weight greater than about 1,000, a secondary charge modifying agent can be used to enhance the cationic charge of the primary charge modifying agent and/or enhance the bonding of the primary charge modifying agent to the microporous surface and/or itself.

The secondary charge modifying agent used in this invention is selected from the group consisting of:
(i) aliphatic amines having at least one primary amine or at least two secondary amine moieties; and
(ii) aliphatic amines having at least one secondary amine and a carboxyl or hydroxyl substituent.

Preferably, the secondary charge modifying agent is a polyamine having the formula:

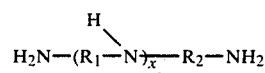

wherein $R_1$ and $R_2$ are alkyl of 1 to 4 carbon atoms and x is an integer from 0 to 4. Preferably, $R_1$ and $R_2$ are both ethyl.

Preferred polyamines are:

| | |
|---|---|
| Ethylene diamine | $H_2N-(CH_2)_2-NH_2$ |
| Diethylene-triamine | $H_2N-(CH_2)_2-NH-(CH_2)_2-NH_2$ |
| Triethylene-tetramine | $H_2N-(CH_2-CH_2-NH)_2-CH_2-CH_2-NH_2$ |
| Tetraethylene-pentamine | $H_2N-(CH_2-CH_2-NH)_3-CH_2-CH_2-NH_2$ |

The highly preferred polyamine is tetraethylene pentamine.

Alternatively, aliphatic amines used in this invention may have at least one secondary amine moiety and a carboxyl or hydroxyl substituent. Exemplary of such aliphatic amines are gamma amino-butyric acid ($H_2NCH_2CH_2CH_2COOH$) and 2-aminoethanol ($H_2NCH_2CH_2OH$).

The secondary charge modifying agent is bonded to the microporous membrane by bonding to a portion of the epoxide substituents of the polymeric primary charge modifying agent.

The amount of primary and secondary cationic charge modifying agent utilized is an amount sufficient to enhance the electropositive capture potential of the microporous membrane. Such an amount is highly dependent on the specific charge modifying agents utilized.

Broadly, the foregoing primary and secondary cationically charge modifying agents are bonded to a hydrophilic organic polymeric microporous membrane, e.g. nylon, by applying to the membrane a charge modifying amount of the primary cationic charge modifying agent bonded to the membrane structure through the epoxide substituent. Preferably, the process comprises (a) contacting the membrane with an aqueous solution of the primary cationic charge modifying agent and (b) contacting the membrane with an aqueous solution of the secondary charge modifying agent. The contacting steps may be performed in any order, i.e. step (a) prior to steb (b) or vice-versa. It is preferred, however, for optimum (minimum) extractables to first contact the membrane with an aqueous solution of the primary cationic charge modifying agent and then subsequently contact the so treated membrane with the aqueous solution of the secondary charge modifying agent.

In another embodiment of the present invention, the foregoing secondary charge modifying agent can be used as the charge modifying agent provided it is bonded to the microporous membrane structure through an aliphatic polyepoxide crosslinking agent having a molecular weight of less than about 500. Preferably, the polyepoxide is a di- or tri-epoxide having a molecular weight of from about 146 to about 300. Such polyepoxides have viscosities (undiluted) of less than about 200 centipoises at 25° C. Due to the necessity of the epoxide to act as a crosslinking agent, monoepoxides, e.g. glycidyl ethers, are unsuitable. Similarly, it is theorized that a polyepoxide offering greater than three epoxy groups offers no benefit and in fact may limit the coupling reactions of the polyepoxide by steric hindrance. Additionally, the presence of unreacted epoxide groups in the cationically charge modified microporous membrane may be undesirable in the finished product.

Highly preferred polyepoxides have the formula:

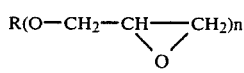

wherein R is an alkyl of 1 to 6 carbon atoms and n is from 2 to 3. The limitation that the number of carbon atoms in the non-epoxide portion—(R)—be less than 6 is so that the polyepoxide will be soluble in water or ethanol-water mixtures, e.g. up to 20% ethanol. While higher carbon content materials are functionally suitable, their application would involve the use of polar organic solvents with resulting problems in toxicity, flammability and vapor emissions.

The aliphatic amino polyamine charge modifying agent can be bonded to the microporous membrane by (a) contacting the membrane with an aqueous solution of the cationic charge modifying agent and (b) contacting the membrane with an aqueous solution of the polyepoxide cross-linking agent. The contacting steps may be performed in any order, i.e. step (a) prior to step (b) or vice-versa. Such contacting steps also include contacting the membrane with an aqueous solution of a mixture of the charge modifying agent and the polyepoxide crosslinking agent. It is preferred, however, for optimum (minimum) flushout times to first contact the membrane with an aqueous solution of the cationic charge modifying agent and then subsequently contact the so treated membrane with the aqueous solution of the polyepoxide crosslinking agent. For maximizing charge modification, however, it is preferred to contact the membrane with an aqueous solution of a mixture of the charge modifying agent and the polyepoxide crosslinking agent.

After the microporous membrane has been contacted with the aqueous solutions, it is then dried and cured, preferably in a restrained condition, to prevent shrinkage.

Drying of the membrane under restraint is described in co-pending U.S. Ser. No. 201,086 to Repetti, filed Oct. 27, 1980. The entire disclosure of this application is incorporated herein by reference. Generally, any suitable restraining technique may be used while drying, such as winding the membrane tightly about a drying surface, e.g. a drum. Bi-axial control is preferred and tensioning the membrane on a stretching frame is considered the most preferred. Preferably, the restraint imposed affects o reduction in dimensions.

Final drying and curing temperatures should be to dry and cure the treated membranes, preferably from about 120° C. to 140° C. for minimmization of drying times without embrittlement or other detrimental effects to the membrane.

The completed membrane may be rolled and stored for use under ambient conditions.

The charge modified microporous membrane can also be employed in the form of a reinforced and/or laminated membrane, preferably one in which a porous reinforcing web is impregnated with a polymeric microporous membrane which is subsequently cationically charged. A preferred reinforced laminated membrane and a porous reinforcing web are described in the aforementioned Barnes et al. application Ser. No. 332,068. Such an impregnated web is preferably produced by casting a sufficient amount of a casting solution onto the porous reinforcing web to provide a web having a coating solution thereon which is then contacted with a quenching bath.

The reinforcing web is a porous material which is preferably wettable by the casting solution to maximize impregnation of the casting solution during casting and become firmly attached to the web during precipitation of the polymeric membrane, e.g. nylon. It is not essential, however, that the web be wettable by the casting solution. If the web is not wettable, the casting solution coating will be largely confined to the surface of the web but is nonetheless adherent thereto due to impregnation of the solution into the web and adhesion of the membrane to the web.

Such wettable and nonwettable reinforcing webs can, for example, be made of nonwoven textiles and cloth, as well as netting of various types, including extruded plastic filament netting, papers and similar materials. Reinforcing webs which are non-wettable by the casting solution may be fine-pored non-woven webs made from fibers, such as polypropylene or polyethylene. Suitable wettable reinforcing webs include polyesters, as nonwoven fibrous webs or woven webs, using monofilaments or multifilament yarn, the monofilaments being preferred in terms of open structure and lower pressure drops; polyamide fiber woven webs, woven and nonwoven webs of aromatic polyamides, and other relatively polar fibrous products such as cellulose, regenerated cellulose, cellulose esters, cellulose ethers, glass fiber and similar materials. Cellulosic and synthetic fiber filter papers may also be used as the reinforcing web as well as perforated plastic sheets and open mesh expanded plastics. If the substrate is relatively coarse or in a very open weave structure, even if the fibers are not substantially wetted by the resin solution, the substrate may nonetheless be impregnated by the membrane material. Thus, such non-wettable materials such as polypropylene and polyethylene can be impregnated by the membrane if they have a sufficiently open structure.

A preferred manner of making the impregnated reinforcing web is by casting a sufficient amount of the casting solution onto the porous reinforcing web to form a web having a coating solution thereon. This coating solution is then calendered, i.e. pressed, preferably by rollers, into the web under conditions of temperature, pressure and time sufficient to reduce the viscosity of the coating solution sufficiently to ensure enhanced penetration of the coating solution into the web and to remove substantially all entrapped air therefrom to thus form a coated web. Such conditions of temperature, pressure and time are highly dependent on the type reinforcing web utilized, the casting solution, type rollers, etc. Such conditions can be readily determined by one skilled in the art by noting the penetration of the solution into the web, and pin holes and bubbles in the final coating. The thus coated web is then subsequently treated by casting a sufficient amount of casting solution thereon to form a coated web having an additional coating solution threon. This so coated web is then quenched in a quenching bath to form the impregnated web to which the outer membranes are then subsequently laminated.

After formation of the reinforced membrane, it can be treated as described hereinabove to produce the cationically charge modified microporous membrane used in this invention.

The cationically charge modified microporous membranes are employed as an immobilizing matrix in macromolecule blotting in the same manner that nitrocellulose and DBM paper has been used heretofore. However, the charge modified microporous membranes of the present invention have a much greater capacity than the immobilizing the matrices used heretofore. For example, it has been found that a charge modified microporous membrane of the present invention has a capacity for binding protein of at least 480 ug/cm$^2$ while nitrocellulose has a capacity of about 80 ug/cm$^2$. It is also not essential to use methanol in the transfer buffer with the immobilizing matrix used in the present invention as is generally the case when nitrocellulose is used. Moreover, nitrocellulose immobilizing matrices, when used in connection with DNA, require high salt concentrations in the buffer; as a result, high current flows of up to 5 amperes are required and the heat generated adversely affects the DNA. The high salt concentrations are not required when using the present charge modified microporous membranes and therefore electrophoresis currents which are in the milliampere range can be employed.

The overlay of the blots (or transferred electropheretograms) can be carried out in the same manner with the immobilized matrix used in the present invention as they have been done in the past with other immobilizing matrices. As in the case of other matrices, the residual potential binding sites on the matrix must be quenched in order to minimize non-specific background. The high affinity of the charge modified microporous membrane used in this invention for proteins means that the normal quenching procedures may not be sufficient. It has been found that the charge modified microporous membranes used in the present invention can be effectively quenched by incubation in 10% bovine serum albumin (BSA) in phosphate buffered saline (PBS) overnight at 45°–50° C. Hemoglobin (1% in PBS at 45°–50° C.) was also found to be effective for quenching the transfers.

While the invention is particularly useful in connection with electrophoretic transfer from chromatographic substrate to matrix, it is also applicable to blotting techniques in general, such as transfer by convection, i.e. mass flow of fluid as a driving force for elution of the macromolecules from the chromatographic substrate to the matrix, and transfer by diffusion.

It is contemplated in accordance with this invention that the cationically charged microporous membrane may be used as an immobilizing matrix for macromolecules derived from not only polyacrylamide or agarose gels but also other chromatographic substrates such as products of thin layer chromatography or high voltage paper electrophoresis or from solutions containing these macromolecules, i.e. directly spotting and to be used for solid phase assays.

Having now generally described this invention, the same will become better understood with reference to certain specific examples, which are included herein for the purpose of illustration only and are not intended to be limiting of the invention.

EXAMPLE I

A.

Preparation of a Microporous Membrane

A representative nylon 66 membrane of 0.22 micrometer nominal rating, having a nominal surface area of about 13m$^2$/g, an Initial Bubble Point of about 47 psi, and a Foam-All-Over-Point of about 52 psi was prepared by the method of Marinaccio et al, U.S. Pat. No. 3,876,738, utilizing a dope composition of 16 percent by weight nylon 66 (Monsanto Vydyne 66B), 7.1% methanol and 76.9% formic acid, a quench bath composition of 25% methanol, 75% water by volume (regenerated as required by the method of Knight et al., U.S. Pat. No. 3,928,517), a casting speed of 24 inches/minute (61 cm/min), and a quench bath temperature of 20° C. The membrane was cast just under the surface of the quench bath by application to a casting drum rotating in the bath (9 to 10 mils as cast wet, to obtain 4.5 to 5.5 mils dry) and allowed to separate from the drum about 90° of arc from the point of application, the self-supporting membrane forming a shallow catenary to takeup. A portion of the uniform opaque film was dried (in restrained condition to resist shrinkage) in a forced air oven at 80°–90° C. for 30 minutes.

B.

Preparation of Charge Modified Microporous Membrane

1. Membrane samples (dried and undried) were dipped in a bath of Hercules 1884 polyamido-polyamine epichlorohydrin resin (4% solids by weight), and allowed to attain adsorption equilibrium. The treated membrane samples were washed to remove excess resin and dried in restrained condition on a drum at a temperature of 110° C. for a period of about 3 minutes.

The treated membrane samples were compared for flow and bubble point characteristics as follows, and found to be essentially identical for treated and untreated samples, evidencing retention of pore and surface geometry. The results are set forth in Table I.

TABLE I

|  | Control (No Treatment) | Undried Membrane | Dried Membrane |
|---|---|---|---|
| Thickness (mils) | 4.25 | 4.58 | 4.83 |
| Initial Bubble Point (psi) | 43.7 | 44.7 | 44.7 |
| Foam-All-Over-Point (psi) | 55.0 | 54.0 | 54.7 |
| Thickness Normalized Flow Rate (cc. mil/min. cm$^2$ .psi) | 7.1 | 7.2 | 7.0 |
| BET, N$_2$ adsorption | 13.12 | — | 13.58 |

The Foam-All-Over-Point (FOAP) is determined by establishing the Initial Bubble Point (IBP) pursuant to ASTM D-2499-66T and then increasing the air pressure until the air flow through the wetted membrane sample, as measured by a flow meter in the line between the regulator and the sample holder, reaches 100 cc/min. FOAP is directly proportional to the mean pore diameter of the sample membrane.

Table I shows, in terms of the morphological and hydrodynamic parameters that control mechanical sieving, the foregoing characteristics of the treated membranes were essentially identical with the untreated nylon membrane.

2. Similar characterizations were conducted on another membrane sample, similarly prepared, but treated with 2% Hercules R 4308 resin (a free radical polymerized resin based upon diallyl nitrogen-containing materials, reacted with epichlorohydrin) in a bath adjusted to pH 10.5, overcoated with 0.1% tetraethylene pentamine, dried, cured, washed and redried. The results are set forth in Table II.

TABLE II

|  | Control (No treatment) | Treated Membrane |
|---|---|---|
| Tensile Strength (psi) |  |  |
| Wet | 528 | 635 |
| Dry | 860 | 960 |
| Elongation (%) |  |  |
| Wet | 140 | 100 |
| Dry | 95 | 40 |

Surface area of the treated and untreated membranes remained essentially unchanged; tensile strength increased with treatment with some loss in elongation. The treated sheet was more flexible; creasing of the untreated sheet resulted in cracking and splitting.

EXAMPLE II

Two layers of wet microporous membrane, made as in Example IA, were laminated together and dried to 20-25% moisture. It has been found that membrane in such a wet, swollen condition absorbs charge modifying agents more efficiently than bone dry membrane.

The double layer of membrane was then introduced into a 1.25% by weight solution of Hercules R 4308. The pH of the bath was 10.5.

This bath was produced by diluting 38 lbs. (17.17 kg.) of Hercules R 4308 resin from its initial 20% by weight concentration to 5%. Five normal (5N) sodium hydroxide solution was then added to raise the pH to 10.5. The solution was then diluted with D.I. water having greater than 150,000 ohm-cm resistivity in a ratio (volume) 2.5:1. The total volume of bath solution was 60 gallons.

The membrane entered the bath of Hercules R 4308 at an angle of 30° from the horizontal to prevent bubble entrapment in the membrane which can prevent the charge modifying agent from diffusing into the membrane. The membrane was treated in this bath at a speed of 2.5 feet/min (76.2 cm/min) for a length of 4 feet (121.9 cm).

Upon exiting this bath, the membrane was wiped on the bottom surface to remove excess water. A three minute air soak with cool air movement was used before the membrane entered the secondary charge modifying agent bath.

This bath was produced by adding 0.023% tetraethylene pentamine by weight or 0.113 lbs. (0.0513 kg.) to 60 gallons (227 liters) of D.I. water (at least 150,000 ohm-cm resistivity). The pH was about 9. The immersion conditions are identical to the first bath of primary charge modifying agent. The membrane was then wrapped around a take-up roll.

The take-up roll of wet membrane was stored for at least 3 hours. The roll was then dried at 250° F. (121° C.) for 3 minutes to complete the reaction of the charge modifying agents.

The membrane was then washed in a subsequent opertion and checked for extraction levels.

EXAMPLE III

Microporous nylon membrane prepared in accordance with Example IA was treated with a Hercules R 4308 primary charge modifying agent (pH of bath adjusted to 10 with sodium hydroxide) and, where indicated, with a polyamine secondary charge modifying agent.

Flow characteristics of the respective membranes showed little or no differentiation, as set forth in Table III:

TABLE III

| Treatment | | | Membrane Characteristics | | |
|---|---|---|---|---|---|
| Charge Modifier | | | IBP | FAOP | Thickness Normalized Flow* (cc. mil$^2$/ |
| Primary | Secondary | Sequence | (psi) | (psi) | min cm$^2$ psi) |
| None | None | — | 48.7 | 52.0 | 6.76 |
| 2.0% | 0.133% Anquamine** | Primary First | 47.3 | 52.3 | 6.76 |
| 2.0% | 0.133% Anquamine | Secondary First | 45.3 | 50.3 | 6.45 |
| 2.0% | 0.133% Anquamine | Mixed | 48.7 | 51.3 | 6.05 |
| 2.0% | None | — | 46.7 | 51.0 | 7.25 |
| 2.0% | 0.03% Tetraethylene | Primary First | 49.5 | 54.0 | 5.80 |

TABLE III-continued

| Treatment | | | Membrane Characteristics | | |
|---|---|---|---|---|---|
| Charge Modifier | | | IBP | FAOP | Thickness Normalized Flow* |
| Primary | Secondary | Sequence | (psi) | (psi) | (cc. mil²/ min cm² psi) |
| Pentamine | | | | | |

\*  $\frac{\text{Flow rate (cc)} \times \text{thickness (mil)}}{\Delta P \text{ (psid)} \times \text{Area (cm}^2\text{)}}$ an empirically derived relation to normalize data for thickness variations.
\*\*Anquamine - 100, a low molecular weight (under 10,000) cationic polyamide adduct evidencing secondary amine functionality by comparative UV spectroanalysis, supplied by Pacific Anchor Chemical Corp.

EXAMPLE IV

In order to compare performance of different primary charge modifiers, particularly polyamide-polyamine epichlorohydrin resin candidates and to optimize application levels and pH conditions, the following tests were conducted, utilizing Hercules resins R 4308, Polycup 172 (pH 4.7 as supplied) and Polycup 2002 (27% solids, pH 3.0 as supplied). The results are set forth in Table IV:

TABLE IV

| Primary Charge Modifier | Bath pH | IBP | FAOP |
|---|---|---|---|
| 1% R 4308 | 10.3 | 47 | 50 |
| 2% R 4308 | 10.3 | 45 | 49 |
| 3% R 4308 | 10.3 | 44 | 51 |
| 1% 172 | 11.0 | 46 | 50 |
| 1% 172 | 4.9 | 47 | 50 |
| 2% 172 | 11.0 | 47 | 52 |
| 2% R 4308 | 11.0 | 47 | 52 |
| 2% 2002 | 11.0 | 49 | 52 |
| Control | — | 46 | 50 |

EXAMPLE V

A washed and stretch dried nylon microporous membrane prepared in accordance with Example I A. was immersed in a two weight percent solid solution of 1,4-butanediol diglycid 1 ether solution prepared with an 80-20 mixture of 18 megohm-cm D.I. water in high purity ethanol and having a pH of 6.1-6.4. The membrane was removed from the solution and allowed to drain for about one minute. The membrane was then immersed in a 0.5 weight percent solid solution of tetraethylene pentamine prepared with 18 megohm-cm D.I. water having a pH of 11.2-11.4. The membrane was removed from the solution, allowed to drain for about one minute and then stretch dried at 130° C. for 5 minutes.

EXAMPLE VI

A nylon impregnated web with a microporous membrane having a nominal pore size rating of about 0.65 microns was produced with a reinforcing web of du Pont Corporation's Reemay 2250 polyester, spun bonded non-woven using a casting solution of 16 weight percent nylon 66, 78.04 weight percent formic acid and 5.96 weight percent methanol. A first outer microporous membrane was brought in contact with the impregnated web to provide a soaking wet contact line at the union of the two layers and a second outer microporous membrane was laid onto the opposite surface of the impregnated web in a similar manner. The three-layer laminated membrane was dried on a Teflon coated steel drum equipped with edge restraining belts on both sides of the laminated membrane and infrared radiant heaters spaced at intervals over the drum circumference. Thereafter, the reinforced laminate was treated with a cationic charge modifier pursuant to Example I B.

EXAMPLE VII

A.

Materials and Methods

Preparation of protein samples:

Erythrocyte ghosts were prepared as described in Fairbanks, G., Steck, T. L. and Wallach, D. F. H. (1971) *Biochemistry* 10: 2606–2617 from blood accumulated in the pleural cavity upon cardiac puncture of anesthesized $CD_1$ mice. Bovine brain cortex homogenates were preared as described in DeCamilli, P., Ueda, T., Bloom, F. E., Battenerg, E., and Greengard, P. (1979) *Proc. Natl. Acad. Sci. U.S.A.:* 76, 5977–5981. The radioiodination of protein standards, protein A, and concanavalin A was performed with 1,3,4,6-tetrachloro-3a,6a-diphenylglycoluril as described in Fraker, P. J., and Speck, J. C. (1978) *Biochem. Biophys. Res. Commun.:* 80, 849–857, except that the proteins were dissolved in PBS (1 mg/ml). Free $^{125}I$ was separated from the $^{125}I$-labeled proteins on either a 5-ml Bio-Gel P-2 column or on a 0.4-ml AG-1-X8 column. The specific activities routinely obtained ranged from $10^6$ to $10^7$ cpm $ug^{-1}$ protein.

Polyacrylamide gel electrophoresis:

Protein samples were solubilized in buffer containing (final concentrations) 2% (w/v) SDS, 2% (v/v) β-mercaptoethanol, 10% (v/v) glycerol, 0.1% (w/v) bromphenol blue, and 100 mM Tris-HCl, pH 6.8. The samples were boiled in this mixture for 3 min. and then resolved, using Laemmli's system, [Laemmli, U.K. (1970) *Nature (London)*: 227, 680–685] on 10% polyacrylamide slab gels.

Electrophoretic transfer:

Upon completion of electrophoresis, the gel (or portions of it) was placed on a wet Scotch-Brite pad and its surface was rinsed with cool (8°–10° C.) transfer buffer (15.6 mM Tris-120 mM glycine, pH 8.3, with or without 20% (v/v) methanol). Tris (41 mM)-boric acid (40 mM), pH 8.3, was also tested. No significant differences were detected between the two buffer systems. The cationically modified microporous membrane of Example II (hereinafter termed "CMMM") or nitrocellulose (hereinafter both are generically referred to as immobilizing matrices "IM") were then wetted by floating it on transfer buffer and placed on the gel, making sure that no air bubbles were caught within the IM or between the latter and the gel. The IM was then covered by a second Scotch-Brite pad. A number of such gel-IM assemblies separated by Scotch-Brite pads can be mounted in sequence for simultaneous transfers. The assembly was placed between plastic grids, which were then snugly inserted—with the IM toward the anode—into a Plexiglas tank containing 4 liters of cool transfer buffer. Platinum electrodes in a configuration similar to that described by Bittner et al., *Anal. Biochem.* (1980): 102, 459–471 were secured to the wide walls of the tank. With an 8-cm distance between the anode and the cathode, the electric field generated during electrophoretic transfer appeared to be homogeneous. During transfer, the buffer composition changed as salts were eluted from the gels, and thus the current increased when the voltage was kept constant. Because a standard power supply was used (Buchler Model 3-1500), it was sometimes found more practical to transfer at constant current (200 mA) and let the voltage gradually decrease. In a typical two hour transfer, the voltage dropped, for instance, from 42 to 30 V. The voltage change could be avoided by prior equilibration of the gels with transfer buffer. This procedure could also prevent gel swelling during transfer, common occurrence at acrylamide concentrations $\geq 10\%$. The IMs could be used immediately after transfer, or dried and stored between sheets of Whatman 3MM chromatography paper. In experiments in which transfer of $^{125}$I-labeled protein was quantitated, both gels and IMs were autoradiographed post-transfer using Kodak XAR-5 film and a DuPont Cronex Lightning Plus intensifying screen at $-70°$ C. The radioactive bands were excised from gels and IMs and counted in a Beckman Biogamma II counter.

Treatment of transfers with antibodies and lectins:

To prevent nonspecific background binding, the IMs must be quenched. For nitrocellulose, it was sufficient to incubate the filters at room temperature for one hour in 10 mM PBS, pH 7.4, containing either 2% (w/v) BSA or 1% (w/v) hemoglobin. Incubation of CMMM IMs in phosphate buffered saline (PBS), containing either 10% BSA or 1% hemoglobin, for 12 hours at $45°-50°$ C. was found satisfactory for quenching. The quenched IMs were reacted with the relevant ligands (e.g., antibodies, protein A, lectins) for one hour at room temperature in PBS containing either 2% BSA or 1% hemoglobin and then washed at least 5 times in 50 to 100 ml PBS (20 min each wash). All solutions used in the overlay procedure contained sodium azide (0.05% w/v). The washed IMs were autoradiographed at $-70°$ C. as described above.

B.

Results

1. Binding of Macromolecules to IMs:

(a) Binding experiments were performed to compare the adsorbence of $^{125}$I-labeled BSA to the IMs. Squares of IM material were incubated for one hour in solutions of variable concentrations of $^{125}$I-labeled BSA (0.01-5% w/v in PBS). Each sample of the incubation medium contained an equal tracer amount of $^{125}$I-labeled BSA (177,000±6100 cpm ml$^{-1}$; estimated amount 180 ng ml$^1$). After incubation, the IMs were washed 5 times with 5 ml PBS and counted. The counts were converted to bound BSA (ug. cm$^{-2}$).

The capacity of the CMMM for binding BSA was consistently higher than that of nitrocellulose. This was particularly evident when high concentrations of BSA were used; at 5% BSA, for instance, the IMs bound 480 ug. cm$^{-2}$ and 80 ug. cm$^{-2}$, respectively. This is shown in FIG. 1 in which the CMMM is designated by ● and the nitrocellulose by ○.

(b) 1 cm$^2$ pieces of CMMM, nitrocellulose, unmodified nylon and the membrane of Example V were incubated in variable concentrations of hemoglobin (0-5% in PBS) or BSA (0-10% in PBS). Each filter was incubated in 1 ml and rotated 2 h RT°c. Then 50 μl of a mixture of $^{125}$I-labeled proteins was added to each well. [50 1=5,000 cpm IgA; 5,000 cpm calmodulin; 5,000 cpm BSA] The filters were thus incubated 1 hr. at 25° C. and then washed 5 times in 1 ml PBS and counted. Background (85 cpm) was subtracted from the results and shown in FIG. 1a (BSA) and 1b (hemoglobin). Note, for example, at 1% BSA, the signal of bound radioactive protein has been reduced to 98%, 48%, 94% and 77% when nitrocellulose CMMM, uncharged nylon and the Example V membrane, respectively, were used. The nonquenched IMs were then washed for about 2 hours in 1% Triton X-100, a non-ionic detergent, to determine how much radioactive protein could be removed. It was found that 40% was removed from the CMMM, about 80% from the IM of Example V, 92% from the uncharged membrane and 92% from the nitrocellulose. These results demonstrate the contribution of the charge modification to the interaction of the proteins with the IMs.

(c) Four Squares (2 cm$^2$) of IMs were spotted with 50,000 cpm of [$^{32}$P] labeled in vitro transcribed human β-globin mRNA (Kole and Weissman, Nucleic Acid Research, 10: 5429 (1982)) and then washed with PBS until the counts in the wash reached background. The amount of labeled mRNA that bound to the filters was then measured. Squares of commercially available nitrocellulose and cellulose acetate bound less than 100 cpm while the two CMMM (0.45 and 0.2 m in porosity) bound about 30,000 cpm.

2. Electrophoretic Transfer of Proteins from Gels to Filters:

The IMs were tested in an electrophoretic transfer (1 hour at 30 V) of $^{125}$I-labeled BSA ($\sim 200$ ng), using buffer conditions similar to those described by Towbin et al. (i.e., 15.6 mM Tris, 120 mM glycine, 20% (v/v) methanol, pH 8.3). When methanol was omitted from the transfer buffer, elution increased from 30% to >60 and ∼50% of the load when CMMM and nitrocellulose were used, respectively. In the absence of methanol, however, $^{125}$I-labeled BSA passed through at least five layers of nitrocellulose (on which it was detected in decreasing amounts, e.g., 15 to 8% of the load); whereas most $^{125}$I-labeled BSA (>60% of the load) could be retained on the first CMMM filter, with <1% detected on each sequential filter. Similar results were obtained with other protein standards (phosphorylase b, fetuin, ovalbumin, carbonic anhydrase, and soybean trypsin inhibitor). A detailed analysis of a representative experiment in which $^{125}$I-labeled BSA was transferred in the absence of methanol is presented in FIGS. 2-4.

FIG. 2 shows quantitation of transfer of variable amounts of $^{125}$I-labeled BSA to CMMM or nitrocellulose. Duplicates of four increasing concentrations of $^{125}$I-labeled BSA (estimated as 150, 300, 514 and 1400 ng) were run on 10% SDS-polyacrylamide gel. After electrophoresis, one series of lanes was transferred to eight sequential layers of CMMM (●, ■, ▲) and the other to 10 sequential layers of nitrocellulose (○, □, △). At the end of the transfer (2 hours in Tris-boric acid, pH 8.3, without methanol, at constant 32 V), the gels and IMs were counted. The amount of BSA eluted from each gel lane (○, ●) was calculated as the difference between radioactivity loaded and radioactivity remaining in the corresponding gel post-transfer. The unaccounted BSA (△, ▲) is the calculated difference between radioactivity eluted from each gel and radioactivity recovered on the corresponding CMMM or nitrocellulose filters (□, ■).

FIG. 3 shows of $^{125}$I-labeled BSA on eight CMMM filters (●) or 10 nitrocellulose filters (○) from the maximal load of BSA (1400 ng) used. Arrow 1 indicates the total amount of recovered on eight layers of CMMM. Arrow 2 indicates the total amount recovered on 10 layers of nitrocellulose.

FIG. 4 shows comparison of BSA recovery on the first CMMM filter, the first nitrocellulose layer, and 10 successive nitrocellulose layers. The results obtained in the experiment presented in FIG. 2 were normalized to the amount of BSA recovered on all eight layers of CMMM for each BSA concentration. This value is taken as 100% recovery. Note that for the three lower concentrations of BSA, the first CMMM layer (striped bars) adsorbed as much as or more than all 10 layers of nitrocellulose (hatched bars). In all cases the amount of BSA recovered on the first CMMM layer was considerably greater (4 times) than that recovered on the first nitrocellulose filter (stippled bars).

FIGS. 2, 3 and 4 show that (i) more than 80% of the protein loaded on the gel could be accounted for when one or two layers of CMMM were used (FIGS. 2 and 3); (ii) 80% (at low load) to 50% (at high load) of the IM bound BSA was recovered on the first layer of CMMM (FIG. 4); and (iii) the use of more than three layers of CMMM did not seem to improve the extent of recovery (FIG. 3). Similar results were not obtained even when 10 layers of nitrocellulose were used (FIGS. 2-4). Unaccounted $^{125}$I-labeled BSA (presumably lost in the buffer) amounted to >25% of the load when nitrocellulose was used and to ≦15% in the case of CMMM.

3. Retention of Transferred Proteins on Filters:

Once adsorbed to CMMM, protein is very well retained, as demonstrated by the results of the following experiments. The $^{125}$I-labeled BSA run on an SDS-polyacrylamide gel was electrophoretically transferred to either CMMM or nitrocellulose. After transfer, the IMs were incubated in one of the following conditions: (i) 15 min in 0.5% glutaraldehyde in PBS, (ii) 1 hr. in 25% isopropanol-10% acetic acid, and (iii) 1 hr. in PBS alone. Next the IMs were rinsed a number of times in PBS and subsequently washed overnight in 0.1% Triton X-100 in PBS. The amount of label on each IM was determined after both transfer and detergent wash. In the case of nitrocellulose, it was found that 80% of the $^{125}$I-labeled BSA was washed away from unfixed IMs; although results were variable, at least 1.5-2 times more counts could be retained on such IMs after the glutaraldehyde or the acidic-alcohol treatments. When CMMM was used, >65% of the original counts were retained in the absence of any fixation and fixation increased this value to >90%. Furthermore, the retention of protein to CMMM seemed practically unaffected by variation in the pH (ranging from 2.0 to 8.3) of the washing solutions.

4. Overlaying of Transfers:

Before one can use a transferred pattern in any overlay technique, residual potential binding sites on the filter must be quenched to minimize nonspecific background. CMMM was quenched effectively when incubated in 10% BSA in PBS overnight at 45°–50° C. Lower temperature (e.g., 37° C.), lower concentrations of BSA, or shorter incubations of the filter with the above solution at 50° C. resulted in unacceptably high background in overlays when these probes were used. Hemoglobin (1% in PBS at 45°–50° C.) was also found to be effective for quenching CMMM transfers.

Overlays of protein patterns were transferred to CMMM or nitrocellulose with antibodies or lectins. In particular, aliquots of bovine brain cortex homogenates (25 ug each) were resolved on a 10% SDS-polyacrylamide gel and electrophoretically transferred to either CMMM or nitrocellulose over two hours in Tris-glycine buffer at 200 mA. After quenching with BSA, the IMs were overlaid for one hour with dilute (1:300) rabbit serum containing anti-protein I (synapsin), washed and subsequently incubated with $^{125}$I-labeled protein A ($10^6$ cpm total) for one hour, washed and then autoradiographed. The same procedure was carried out using aliquots of murine erythrocytic ghosts (25 ug each), filters quenched with hemoglobin and $^{125}$I-labeled concanavalin A ($5 \times 10^5$ cpm total) as the probe. The greater binding capacity of CMMM over nitrocellulose rendered these techniques more sensitive when CMMM is used.

The specificity of lectin binding was tested by using appropriate haptens. In the case of the autoradiographs of the $^{125}$I-labeled concanavalin A, for instance, the net radioactivity bound to the respective IMs was determined by deducting from the total counts the background counts measured on the lower parts of the lanes. The net signal on CMMM was 1.6 times higher than on nitrocellulose. A first wash in PBS containing 100 mM α-methylglucoside removed 82 and 76% of the signal from CMMM and nitrocellulose, respectively. A second wash in PBS containing 100 mM α-methylmannoside increased the removal to 90% for CMMM and 84% for nitrocellulose.

The acetylcholine receptor has also been analyzed by protein blotting. Electric organ membranes prepared from Torpedo were run at 4° C. on polyacrylamide gels containing lithium dodecyl sulfate. The electrophoretograms were electroblotted to CMMM, which were then quenched with hemoglobin and overlaid with $^{125}$I-labeled α-bungarotoxin. Only the α-subunit of the receptor bound the toxin. This binding could be competed with nonradioactive α-bungarotoxin and with tubocurarine, another acetylcholine antagonist.

Various changes and modifications can be made in the process and products of this invention without departing from the spirit and scope thereof. The various embodiments which have been disclosed herein were for the purpose of further illustrating the invention, but were not intended to limit it.

What is claimed is:

1. A product comprising a chromatographic substrate having on a surface thereof as an immobilizing matrix a hydrophilic charge modified microporous membrane comprising an organic microporous membrane having a charge modifying amount of a cationic charge modifying agent bonded to substantially all of the surfaces of said membrane wetted by a fluid passing through said membrane or in which said membrane is immersed.

2. The product of claim 1, wherein the organic microporous membrane is hydrophilic.

3. The product of claim 2, wherein the hydrophilic organic polymeric microporous membrane is a cellulose ester.

4. The product of claim 2, wherein the hydrophilic organic polymeric microporous membrane is a polyamide.

5. The product of claim 2, wherein the charge modifying agent comprises a water-soluble organic polymer having a molecular weight greater than about 1,000, wherein each monomer thereof has least one epoxide group capable of bonding to the surface of the membrane and at least one tertiary amine or quaternary ammonium group.

6. The product of claim 5, wherein said water-soluble organic polymer is a polyamido-polyamine epichlorohydrin resin.

7. The macromolecule blotting product of claim 6 is a polymer having repeating monomer units of the formula:

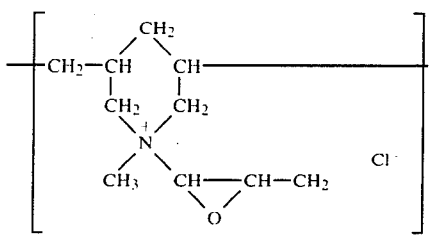

8. The product of claim 7, wherein said membrane is polyhexamethylene adipamide.

9. The product of claim 8, wherein said substrate is an electrophoresis gel.

10. The product of claim 9, wherein said gel comprises polyacrylamide.

11. The product of claim 5, wherein a portion of the epoxy groups of the organic polymer charge modifying agent are bonded to a secondary charge modifying agent selected from the group consisting of:
   (i) aliphatic amines having at least one primary amino or at least two secondary amino groups; and
   (ii) aliphatic amines having at least one secondary amino and a carboxyl or hydroxyl substituent.

12. The product of claim 11, wherein said secondary charge modifying agent is tetraethylenepentamine.

13. The product of claim 12, wherein said substrate is an electrophoresis gel.

14. The product of claim 2, wherein said charge modifying agent is selected from the group consisting of:
   (i) aliphatic amines having at least one primary amino or at least two secondary amino groups; and
   (ii) aliphatic amines having at least one secondary amino and a carboxyl or hydroxyl substituent, and wherein said charge modifying agent is bonded to the microporous membrane structure through an aliphatic polyepoxide crosslinking agent having a molecular weight of less than about 500.

15. The product of claim 14, wherein the polyepoxide is 1,4-butanediol diglycidal ether.

16. The product of claim 15, wherein said charge modifying agent is tetraethylenepentamine.

17. The product of claim 16, wherein said substrate is an electrophoresis gel.

18. The product of claim 4, wherein the membrane has a pore size of from about 0.05 to about 1.2 microns.

19. In a method for the transfer of macromolecule from a chromatographic substrate to an immobilizing matrix, the improvement which comprises employing as said matrix, a hydrophilic charge modified microporous membrane comprising an organic microporous membrane having a charge modifying amount of a cationic charge modifying agent bonded to substantially all of the surfaces of said membrane wetted by a fluid passing through said membrane or in which said membrane is immersed.

20. The method of claim 19, wherein said organic microporous membrane is hydrophilic.

21. The method of claim 20, wherein the hydrophilic organic polymeric microporous membrane is a cellulose ester.

22. The method of claim 20, wherein the hydrophilic organic polymeric microporous membrane is a polyamide.

23. The method of claim 22, wherein the charge modifying agent comprises a water-soluble organic polymer having a molecular weight greater than about 1,000, wherein each monomer thereof has least one epoxide group capable of bonding to the surface of the membrane and at least one tertiary amine or quaternary ammonium group.

24. The method of claim 23, wherein said water-soluble organic polymer is a polyamido-polyamine epichlorohydrin resin.

25. The method of claim 24, wherein said polymer has repeating monomer units of the formula:

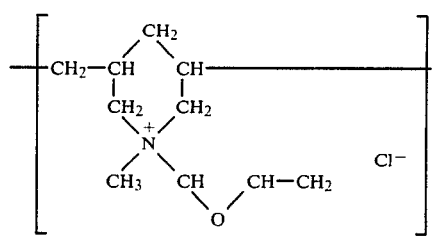

26. The method of claim 25, wherein said membrane is a polyhexamethylene adipamide.

27. The method of claim 25, wherein said substrate is an electrophoresis gel.

28. The method of claim 27, wherein said gel comprises polyacrylamide.

29. The method of claim 23, wherein a portion of the epoxy groups of the organic polymer charge modifying agent are bonded to a secondary charge modifying agent selected from the group consisting of:
   (i) aliphatic amines having at least one primary amino or at least two secondary amino groups; and
   (ii) aliphatic amines having at least one secondary amino and a carboxyl or hydroxyl substituent.

30. The method of claim 29, wherein said secondary charge modifying agent is tetraethylenepentamine.

31. The method of claim 30, wherein said substrate is an electrophoresis gel.

32. The method of claim 20, wherein said charge modifying agent is selected from the group consisting of:
   (i) aliphatic amines having at least one primary amino or at least two secondary amino groups; and
   (ii) aliphatic amines having at least one secondary amino and a carboxyl or hydroxyl substituent, and wherein said charge modifying agent is bonded to the microporous membrane structure through an aliphatic polyepoxide crosslinking agent having a molecular weight of less than about 500.

33. The method of claim 32, wherein the polyepoxide is 1,4-butanediol diglycidal ether.

34. The method of claim 33, wherein said charge modifying agent is tetraethylenepentamine.

35. The method of claim 20, wherein said substrate is an electrophoresis gel.

36. The method of claim 22, wherein the membrane has a pore size of from about 0.05 to about 1.2 microns.

37. The method of claim 20, wherein the transferred protein is incubated with a ligand.

38. The method of claim 37, wherein the charge modified microporous membrane is quenched after transfer of the protein and before incubation with the ligand.

39. The method of claim 38, wherein the quenching is effected by incubating the membrane with bovine serum albumin or hemoglobin at elevated temperature.

40. The method of claim 22, wherein said transfer is by electroelution.

41. In a solid phase assay system wherein a macromolecule is immobilized in the solid phase, the improvement which comprises employing as said solid phase, a hydrophilic charge modified microporous membrane comprising an organic microporous membrane having a charge modifying amount of a cationic, charge modifying agent bonded to substantially all of the surfaces of said membrane wetted by a fluid passing through said membranes or in which said membrane is immersed.

42. The system of claim 41, wherein said organic microporous membrane is hydrophilic.

43. The system of claim 42, wherein the hydrophilic organic polymeric microporous membrane is a cellulose ester.

44. The system of claim 42, wherein the hydrophilic organic polymeric microporous membrane is a polyamide.

45. The system of claim 43, wherein the charge modifying agent comprises a water-soluble organic polymer having a molecular weight greater than about 1,000, wherein each monomer thereof has at least one epoxide group capable of bonding to the surface of the membranes and at least one tertiary amine or quaternary ammonium group.

46. The system of claim 44, wherein said water-soluble organic polymer is a polyamido-polyamine epichlorohydrin resin.

47. The system of claim 46, wherein said polymer has repeating monomer units of the formula:

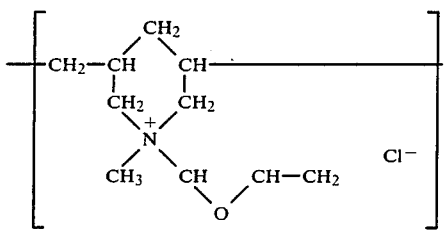

48. The system of claim 47, wherein said membrane is a polyhexamethylene adipamide.

49. The system of claim 45, wherein a portion of the epoxy groups of the organic polymer charge modifying agent are bonded to a secondary charge modifying agent selected from the group consisting of:
  (i) aliphatic amines having at least one primary amino or at least two secondary amino groups; and
  (ii) aliphatic amines having at least one secondary amino and a carboxyl or hydroxyl substituent.

50. The system of claim 49, wherein said secondary charge modifying agent is tetraethylenepentamine.

51. The system of claim 41, wherein said charge modifying agent is selected from the group consisting of:
  (i) aliphatic amines having at least one primary amino or at least two secondary amino groups; and
  (ii) aliphatic amines having at least one secondary amino and a carboxyl or hydroxyl substituent, and wherein said charge modifying agent is bonded to the microporous membrane structure through an aliphatic polyepoxide crosslinking agent having a molecular weight of less than about 500.

52. The system of claim 51, wherein the polyepoxide is 1,4-butanediol diglycidal ether.

53. The system of claim 52, wherein said charge modifying agent is tetraethylenepentamine.

54. The system of claim 42, wherein the charge modified miciroporous membrane is a quenched membrane.

* * * * *

UNITED STATES PATENT AND TRADEMARK OFFICE
CERTIFICATE OF CORRECTION

PATENT NO. : 4,512,896
DATED : April 23, 1985
INVENTOR(S) : Jonathan M. Gershoni It is certified that error appears in the above-identified patent and that said Letters Patent are hereby corrected as shown below:

Please add to the specification at Column 1, line 7, after BACKGROUND OF THE INVENTION:
-- This invention was made with Government support under NIH Grant No. GM27303. The Government has certain rights in this invention. --

Signed and Sealed this

Fifth Day of November 1985

[SEAL]

Attest:

Attesting Officer

DONALD J. QUIGG

Commissioner of Patents and Trademarks